US00PP14701P29

(12) United States Plant Patent
Fross

(10) Patent No.: US PP14,701 P2
(45) Date of Patent: Apr. 13, 2004

(54) GERANIUM PLANT NAMED 'CHERYL'S SHADOW'

(50) Latin Name: *Geranium×hybrida*
Varietal Denomination: Cheryl's Shadow

(76) Inventor: David C. R. Fross, 379 W. El Campo Rd, Arroyo Grande, CA (US) 93420

( * ) Notice: Subject to any disclaimer, the term of this patent is extended or adjusted under 35 U.S.C. 154(b) by 26 days.

(21) Appl. No.: 10/430,131

(22) Filed: May 6, 2003

(51) Int. Cl.[7] ..... A01H 5/00
(52) U.S. Cl. ..... Plt./324
(58) Field of Search ..... Plt./324

*Primary Examiner*—Kent Bell

(57) ABSTRACT

A new cultivar of Geranium plant named 'Cheryl's Shadow' that is characterized by small pale pink flowers against contrasting dark purple foliage, rose-pink stems, and prostrate habit. In combination these traits set 'Cheryl's Shadow' apart from all other varieties of Geranium known to the inventor.

2 Drawing Sheets

Genus: Geranium.
Species: ×hybrida.
Denomination: Cheryl's Shadow.

BACKGROUND OF THE INVENTION

The present invention relates to a new and distinct cultivar of Geranium known botanically as Geranium ×hybrida and hereinafter referred to by the cultivar name 'Cheryl's Shadow'. The new variety 'Cheryl's Shadow' is a perennial hybrid plant grown for use in containers and in the landscape as an ornamental.

'Cheryl's Shadow' was discovered by the inventor as a chance seedling that resulted from open pollination occurring in a cultivated area of Arroyo Grande, Calif. The seedling 'Cheryl's Shadow' was selected in 1999 for its dark purple foliage and contrasting pale pink flowers. 'Cheryl's Shadow' was discovered as one individual seedling among other Geraniums in a block of mother stock. The block of mother stock was made up of the following different individual crops of Geraniums that were being evaluated for commercial production: Geranium 'Bertie Crug', Geranium "Crug Strain Seedlings", *Geranium sessiliflorum* ssp. *novaezelandiae* 'Nigricans', *Geranium traversii* var. *elegans* 'Porters Pass', and Geranium 'Stanhoe' (all unpatented).

'Cheryl's Shadow' is a Geranium characterized by low-growing habit, dark purple leaves, rose-pink stems and small pale pink flowers. The exact parents are unidentified, however the female parent is presumed to be *Geranium traversii* var. *elegans* 'Porters Pass' (unpatented). 'Cheryl's Shadow' is distinguishable from 'Porters Pass' by flower color. 'Porters Pass' exhibits white flowers whereas 'Cheryl's Shadow' exhibits pale pink flowers. Geranium 'Pink Spice' (U.S. Plant Pat. No. 12,172) is the closest comparison plant to 'Cheryl's Shadow'. When compared with 'Pink Spice', 'Cheryl's Shadow' exhibits smaller leaves, dark purple foliage, open rosette branching, small pale pink flowers, and a low spreading habit.

In 2001 the inventor conducted the first asexual propagation in a cultivated area of Arroyo Grande, Calif. using the method of stem cuttings. Since that time subsequent asexual propagation has been conducted using stem cuttings, tissue culture and division. Under careful observation the instant plant has been determined stable and uniform and reproduces true to type in successive generations.

SUMMARY OF THE INVENTION

The following traits have been repeatedly observed and represent the distinguishing characteristics of the new Geranium plant 'Cheryl's Shadow'. These traits in combination distinguish 'Cheryl's Shadow' from all other varieties of Geranium known to the inventor. The new invention has not been tested under all possible conditions and phenotypic differences may be observed with variations in environmental, climatic, and cultural conditions, however, without any variance in genotype.

1. Geranium 'Cheryl's Shadow' exhibits a low-growing, prostrate habit.
2. Geranium 'Cheryl's Shadow' exhibits small pale pink flowers.
3. Geranium 'Cheryl's Shadow' exhibits rose-pink stems.
4. Geranium 'Cheryl's Shadow' begins blooming in late spring and continues blooming through the summer months.
5. Geranium 'Cheryl's Shadow' is 6 cm. in height and 31 cm. in width in a 1-litre container.
6. Propagation of Geranium 'Cheryl's Shadow' can be accomplished by using stem cuttings, tissue culture and division.
7. Geranium 'Cheryl's Shadow' exhibits dark purple foliage.
8. Geranium 'Cheryl's Shadow' is hardy to USDA Zone 5.

BRIEF DESCRIPTION OF THE DRAWINGS

The accompanying color drawings illustrate the overall appearance of the new variety 'Cheryl's Shadow' showing the colors as true as is reasonably possible to obtain in colored reproductions of this type. The plant in the drawing on sheet 1 is 6 to 8-months-old and was initially transplanted from a 1-litre container into the ground. The plant is growing out-of-doors in Newport Beach, Calif. and measures 21 cm. in height and 70 cm. in width. The plant in the drawing on sheet 2 is a 4-month-old plant in a 1-litre container grown out-of-doors in Arroyo Grande Calif. Colors in the photographs may differ from the values cited in the detailed botanical description, which accurately describe the actual colors of the new variety 'Cheryl's Shadow'.

The drawing on sheet 1 shows the plant from a side perspective.

The drawing on sheet 2 is a close-up view of the flower on 'Cheryl's Shadow'. All photographs are taken using conventional photographic techniques and although colors may appear different from actual colors due to light reflectance, they are as accurate as possible by conventional photography.

BOTANICAL DESCRIPTION OF THE PLANT

The following is a detailed description of the new Geranium cultivar 'Cheryl's Shadow'. Data was collected in Arroyo Grande Calif. from 4-month-old plants grown out-of-doors in 1-litre containers. Color determinations are in accordance with The Royal Horticultural Society Colour chart except where general color terms of ordinary dictionary significance are used. The growing requirements are similar to the species and no disease problems have been observed.

Botanical classification: Geranium 'Cheryl's Shadow'.
Species: ×hybrida.
Parentage: 'Cheryl's Shadow' is a chance seedling that resulted from open pollination. The exact parents are unidentified.
- *Presumed female parent.*—*Geranium traversii* var. *elegans* 'Porters Pass'.
- *Male parent.*—Unidentified Geranium hybrid.

Common names: Cranesbill and Geranium.
Type: Perennial.
Hardiness: USDA Zone 5.
Use: Border, groundcover for the landscape or container plant.
Growth: Vigorous grower.
Roots: Fibrous roots.
Growth habit: Prostrate.
Height: 6 cm. in height in a 1-litre container.
Width: 31 cm. in width in a 1-litre container.
Branching habit: Open rosette.
Flowering time: Diurnal.
Flowering season: Pale pink flowers begin blooming in late spring and continue through summer.
Propagation method: Propagated by stem cuttings, tissue culture and division.
Special needs: Cut back after flowering to induce fresh flush of foliage and flowers.
Soil: Tolerant of a range of soil types, but generally needs moderately fertile, retentive soil.
Light levels: Plant in full sun or part shade.
Crop time: 4–5 months are needed to produce a finished 1-litre container from a rooted cutting or division.
Rooting time: 3 weeks are needed for an initial cutting to produce roots.
Susceptibility to pests and disease: No known susceptibility to pests or diseases observed to date.
Stem:
- *Stem shape.*—Oval.
- *Stem color.*—177B.
- *Stem surface.*—Pubescent.
- *Stem dimensions.*—14 cm. in length and 3 mm. in diameter.
- *Internode length.*—Ranges from 1 cm. to 2 cm. in length.

Foliage:
- *Leaf arrangement.*—Terminal.
- *Leaf division.*—Palmately divided.
- *Leaf shape.*—Closest to reinform.
- *Leaf base.*—Auriculate.
- *Leaf margins.*—Lobed and crenate.
- *Leaf apex.*—A combination of truncate and lobed on each individual leaf.
- *Leaf venation.*—Pinnipalmate.
- *Vein color* (*abaxial surface*).—N186B.
- *Vein color* (*abaxial surface*).—197A.
- *Leaf surface* (*abaxial*).—Pubescent.
- *Leaf surface* (*abaxial*).—Pubescent.
- *Leaf appearance* (*adaxial surface*).—Dull appearance.
- *Leaf appearance* (*abaxial surface*).—Shiny appearance.
- *Leaf dimensions* (*mature*).—2.5 cm. in length and 3 cm. in width.
- *Leaf dimensions* (*young*).—1.5 cm. in length and 1.5 cm. in width.
- *Quantity of leaves.*—One per stem.
- *Young leaf color* (*adaxial surface*).—N187A.
- *Young leaf color* (*abaxial surface*).—197A.
- *Mature leaf color* (*adaxial surface*).—N187A.
- *Mature leaf color* (*abaxial surface*).—197A.
- *Petiole surface.*—Pubescent.
- *Dimensions of petiole.*—8–10 cm. in length and 2 mm. in width.
- *Petiole shape.*—Cylindrical.
- *Color of petiole.*—182B.
- *Stipules.*—None observed.
- *Foliar fragrance.*—None present.

Flower:
- *Flower form.*—Single form.
- *Flower arrangement.*—1-flowered.
- *Flower shape.*—Rotate.
- *Flower dimensions.*—1.50 cm. in diameter and 0.50 cm. in height.
- *Aspect.*—Facing upward.
- *Self-cleaning or persistent.*—Self-cleaning.
- *Flower color.*—Both colors 75C and 75D are individually present on an individual flower.
- *Petals.*—Five in number.
- *Petal dimensions.*—5 mm. in width and 7 mm. in length.
- *Petals fused or unfused.*—Unfused.
- *Petal margin.*—Entire.
- *Petal apex.*—Obtuse.
- *Petal base.*—Attenuate.
- *Petal shape.*—Closest to obdeltoid but with a longer elongated base.
- *Petal surface* (*abaxial and adaxial surfaces*).—Glabrous.
- *Petal color* (*adaxial surface*).—The majority of an individual petal surface is both individual colors 75C and 75D. The base of the petals range in color from 155C to 145D with veins that are 145C in each individual flower.
- *Petal color* (*abaxial surface*).—The majority of an individual petal surface is both individual colors 75C and 75D. The base of the petals range in color from 155C to 145D with veins that are 145C in each individual flower.
- *Bud color.*—75B.

*Bud shape.*—Ovate.
*Bud surface.*—Pubescent.
*Bud dimensions.*—7 mm. in length and 5 m. in width.
*Sepals.*—Five in number.
*Sepal dimensions.*—8–9 mm. in length and 4 mm. in width.
*Sepal margin.*—Entire.
*Sepal surface.*—Lanate.
*Sepal shape.*—Oval.
*Sepals fused or unfused.*—Unfused.
*Sepal apex.*—Aristate.
*Sepal base.*—Attenuate.
*Sepal color* (*adaxial and abaxial surfaces*).—N186B.
*Peduncle shape.*—Cylindrical.
*Peduncle surface.*—Pubescent.
*Peduncle dimensions.*—2 cm. in length and 1.5 mm. in width.
*Peduncle color.*—199D.
*Flower fragrance.*—None observed.

Reproductive organs:
*Stamens.*—Five stamens united at base.
*Stamen color.*—155A.
*Stamen dimensions.*—4 mm. in length and 1 mm. in width.
*Pistil.*—One.
*Pistil shape.*—Inflated.
*Pistil color.*—155A.
*Pistil dimensions.*—4 mm. in height and 1 mm. in width.
*Pollen.*—None observed to date.
*Anther.*—None observed to date.
*Stigma shape.*—Forked.
*Stigma color.*—29D.
*Stigma dimensions.*—2 mm. in length and 3 mm. in diameter.
*Ovary position.*—Superior.
*Ovary color.*—144D.
*Ovary shape.*—Globose.
*Ovary dimensions.*—2 mm. in height and 2 mm. in diameter.

Seed: No seed has been observed by the inventor to date.

I claim:

1. A new and distinct variety of Geranium plant named 'Cheryl's Shadow' as described and illustrated herein.

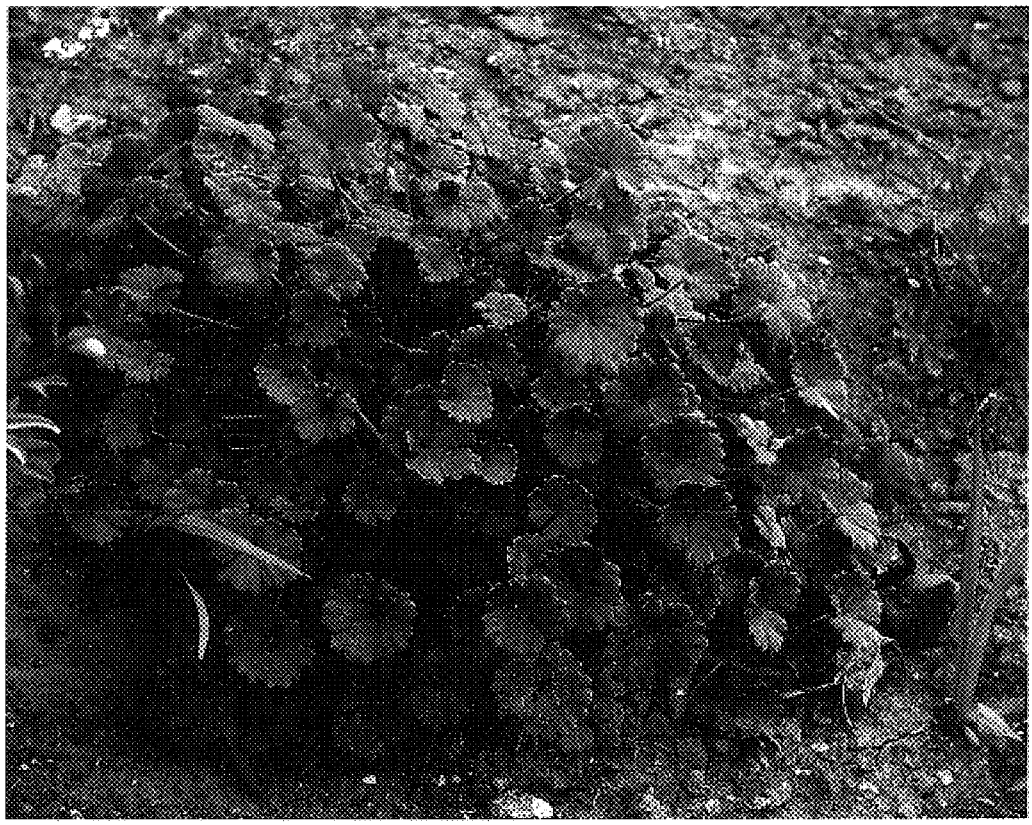

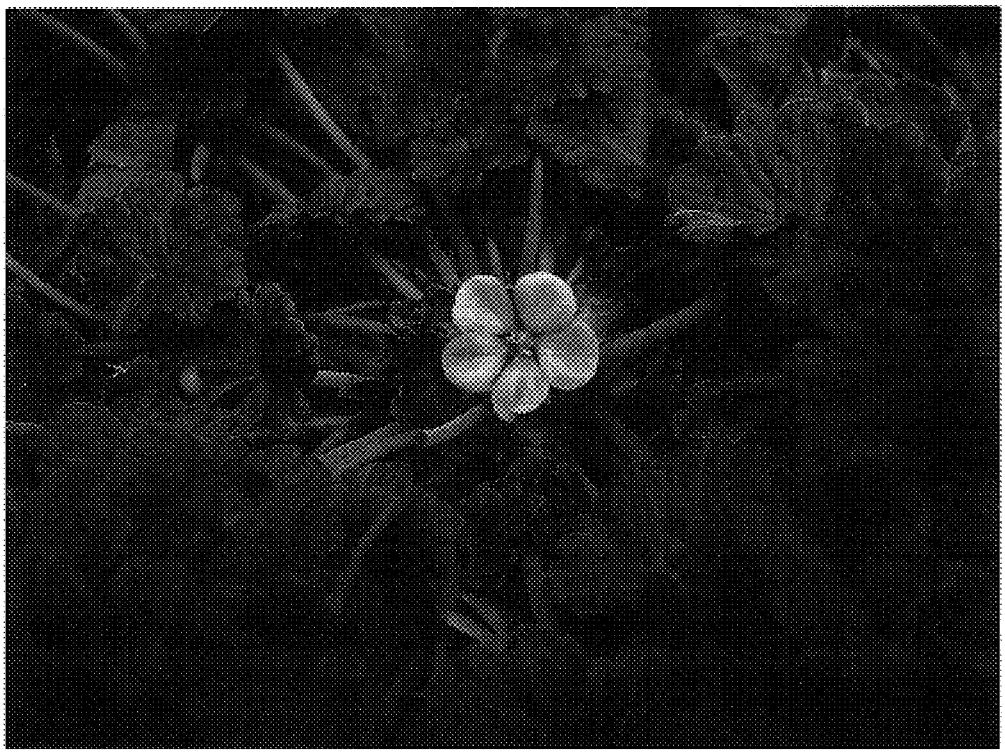

* * * * *